(12) United States Patent
Scott

(10) Patent No.: US 6,766,185 B2
(45) Date of Patent: Jul. 20, 2004

(54) TRANSMISSION LINE TECHNIQUES FOR MRI CATHETER COIL MINIATURIZATION AND TUNING

(75) Inventor: Greig C. Scott, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 254 days.

(21) Appl. No.: 09/863,797

(22) Filed: May 22, 2001

(65) Prior Publication Data

US 2002/0013525 A1 Jan. 31, 2002

Related U.S. Application Data

(60) Provisional application No. 60/206,458, filed on May 22, 2000.

(51) Int. Cl.$^7$ .............................................. A61B 5/055
(52) U.S. Cl. ...................... 600/410; 600/423; 324/318; 324/322; 29/828
(58) Field of Search ................................ 600/422, 423, 600/410; 324/318, 322; 29/825, 828, 832

(56) References Cited

U.S. PATENT DOCUMENTS 4,881,034 A * 11/1989 Kaufman et al. ........... 324/318
5,347,221 A * 9/1994 Rubinson .................... 324/318
5,432,451 A * 7/1995 McGill et al. .............. 324/322
6,263,229 B1 * 7/2001 Atalar et al. ................ 600/423
6,437,569 B1 * 8/2002 Minkoff et al. ............. 324/318

* cited by examiner

Primary Examiner—Ruth S. Smith
(74) Attorney, Agent, or Firm—Lumen Intellectual Property Services, Inc.

(57) ABSTRACT

A device and method with miniature and tunable MRI receiver coil for catheters is provided that can be used in minimally invasive procedures and intravascular imaging. An MRI receiver coil for catheter procedures is provided having an impedance matching element that includes at least one miniature transmission line cable which are interconnected to construct the impedance matching element. In a particular embodiment, the miniature transmission line cables are constructed to make an inductance matching element defining an inductance L. In another particular embodiment, the miniature transmission line cable is a capacitance matching element defining a capacitance C. The present invention provides a system and method that allows local fine-tuning with a higher signal-to-noise ratio. Transmission line cables also overcome the minimum size limits of fixed components. The shielded and balance techniques further reduce noise and improve safety.

34 Claims, 4 Drawing Sheets

TRANSMISSION LINE TECHNIQUES FOR MRI CATHETER COIL MINIATURIZATION AND TUNING

CROSS-REFERENCE TO RELATED APPLICATIONS

This application is cross-referenced to and claims priority from U.S. Provisional application 60/206,458 filed May 22, 2000, which is hereby incorporated by reference.

STATEMENT REGARDING FEDERALLY SPONSORED RESEARCH OR DEVELOPMENT

This invention was supported in part by grant from the National Institutes of Health under grant number 1R01HL61864. The Government has certain rights in the invention.

FIELD OF THE INVENTION

This invention relates generally to magnetic resonance imaging (MRI). More particularly, the present invention relates to a device and method for MRI receiver coil miniaturization and tuning.

BACKGROUND

In vivo imaging of arterial plaques poses a significant challenge for resolution and signal-to-noise. Conventional magnetic resonance imaging (MRI) uses receiver coils placed on the surface of or surrounding the body to attain resolutions on the order of 1–5 mm. Important anatomical information for arterial plaques, for instance, can be obtained if the resolution can be extended to 100–500 $\mu$m. Since the voxel volumes will be 100 times smaller, the coil must provide a significant boost in sensitivity. This can be achieved using intravascular receiver coils-micro-coils that are inserted by catheters to the arterial plaque.

Several design issues are unique to intravascular coil design. First, the coil, matching network and cable must be small enough and flexible enough to pass through larger vessels to the target region without undue trauma to the vessel. The probe cannot completely block blood flow nor dislodge the plaque. Blood flow will subject the probe to motion or vibration a problem that is reduced by real-time MRI. Secondly, the relative orientation of the target artery with respect to the main magnetic field limits the coil configuration that can generate a B1 field local to the plaque. This orientation can be unpredictable for tortuous vessels such as the coronaries or aortic artery arch, but quite simple for vessels such as the carotids, iliofemoral and popliteal which are oriented mainly along the head to foot axes. Finally, the region of interest lies outside the coil, inspiring the term, inside-out MRI.

The signal and noise tradeoffs and design principles for MRI receiver coils are well understood. To detect an MRI signal, a coil must be capable of generating an RF magnetic field component B1 orthogonal to the static field component B0. According to reciprocity, the B1 spatial behavior determines the sensitivity profile of the coil. The peak B1 scales inversely with coil radius but also diminishes outside the coil over a similar size scale.

The prior art describes several catheter coils such as, for instance, opposed solenoids, miniaturized versions of saddle and surface (loops) coils, multiple coils, shortened twin lead designs and dipole antenna designs. In conventional systems, tissue conductivity inductively couples with the receiver coil to generate a resistance, hence noise, that scales approximately with the field of view volume seen by the coil. In the case of a surface coil, which is a simple tuned copper loop 3 to 5 inches in diameter, the depth of sensitivity is limited approximately to the coil diameter. Such a coil could image an artery 2.5 inches deep, but couples so much tissue noise that the resolution is inadequate for plaque imaging.

For very small coils, the resistance becomes vanishingly small, and the wire resistance of the coil becomes the dominant noise source. The resistance varies inversely with the coil quality factor Q which tends to be fixed by size and geometry. One can increase the number of turns N to maintain coil size without adverse changes in Q or sensitivity. Furthermore, Q is optimized when the turn spacing is about equal to wire radius. Unfortunately, small coils with many turns or in close proximity to tissue have an associated quasi-static electric field that fringes into the tissue. The fringe field creates an extra resistance due to dielectric loss that can significantly degrade signal-to-noise-ratio. In standard MRI coils, the electric fields are minimized by splitting the coil into segments with extra series capacitors but this becomes impractical in small coils.

Accordingly, there is a need to overcome current problems for constructing catheter MRI coils that can be used in minimally invasive procedures and intravascular imaging.

SUMMARY OF THE INVENTION

The present invention provides a device and method for miniature and tunable MRI receiver coil for catheters that can be used in minimally invasive procedures and intravascular imaging. An MRI receiver coil for catheter procedures is provided having an impedance matching element. The impedance matching element includes at least one miniature transmission line cable which is interconnected to construct the impedance matching element. In the present invention transmission line cables could also be miniature coaxial cables. In a particular embodiment, the miniature transmission line cables are constructed to make an inductance matching element defining an inductance L. In another particular embodiment, the miniature transmission line cable is a capacitance matching element defining a capacitance C. Furthermore, the present invention includes adjusting the length of at least one miniature transmission line cable to adjust capacitance C of the capacitance matching element. In addition, the present invention includes adjusting the length of at least one miniature transmission line cable to adjust inductance L of the inductance matching element. The present invention includes various different geometries of connecting the miniature transmission line cables or miniature coaxial cables. For instance, the miniature transmission line cables could be connected in series or in parallel. In addition, the miniature transmission line cables could be connected at one end or at both ends. The miniature transmission line cables could also be construed as an open circuit or a closed circuit. Furthermore, the various connections could be surrounded by a shielded element. The impedance matching element comprises conductive thin film layers to form electrically shielded structures or Faraday shields. These electrically shielded structures are, for instance, but not limited to, constructed of silver paint and coaxial shields. The impedance matching element also incorporates balanced transmission lines to prevent common mode current. Furthermore, the present invention includes a fine-tuning element that includes at least one miniature transmission line and which is placed in series with the impedance matching element and connected at both ends. The fine-tuning element could have different electrical properties. In addition, the fine-tuning element could be placed remotely from the area of interest. The present invention also provides the method of constructing an MRI receiver coil for catheter procedures that has an impedance matching element. The method steps for constructing such a MRI receiver coil include the trimming of at least one miniature transmission line cable and subsequently connecting the trimmed miniature transmission line cables to construct the impedance matching element.

In view of that which is stated above, it is the objective of the present invention to provide miniature and tunable MRI receiver coils for catheters in minimally invasive procedures and intravascular imaging.

It is another objective of the present invention to overcome standard component size limits for constructing catheter MRI coils.

It is yet another objective of the present invention to augment or replace lumped capacitors and inductors with transmission line cables or micro-coaxial cables that can be trimmed to arbitrary length yielding adjustable component values.

It is still another objective of the present invention to provide short circuit or open circuit transmission lines stubs.

It is still another objective of the present invention to provide flexible MRI receiver coils that have small cross-section diameter so that they can be used in minimally invasive MRI procedures.

It is another objective of the present invention to use conductive thin film layers to form electrically shielded structures for intravascular/catheter MRI coils.

It is another objective of the present invention to shield the patient and probe from each other and to form a structure that prevents dangerous common mode current and reduces noise.

It is another objective of the present invention to provide series connected lines that allow for coil tuning to be approximately tuned with fine tuning placed remotely in larger cross-sectional areas.

Most prior art designs use fixed capacitors and must include fine-tuning adjustments about 1.5 meter away from the probe. Capacitors do not come in custom sizes for tuning. The advantage of the present invention over the prior art is that the system and method enables one to include transmission line stubs that allow fine-tuning locally with a higher signal-to-noise ratio. Transmission line stubs also overcome the minimum size limits of fixed components. The shielding and balance techniques further reduce noise and improve safety.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a device and method for miniature and tunable MRI receiver coil for catheters that can be used in minimally invasive procedures and intravascular imaging. In the present invention, lumped capacitors and inductors are replaced or augmented with transmission line cables that can be trimmed to arbitrary length yielding adjustable component values. These transmission line cables appear either as short circuit or open circuit transmission line stubs. They have small cross-sectional diameter and are flexible so they can be used in minimally invasive MRI procedures. A transmission line cable is, for instance, but not limited to, a miniature coaxial cable or a balanced shielded line.

Figure 1A:
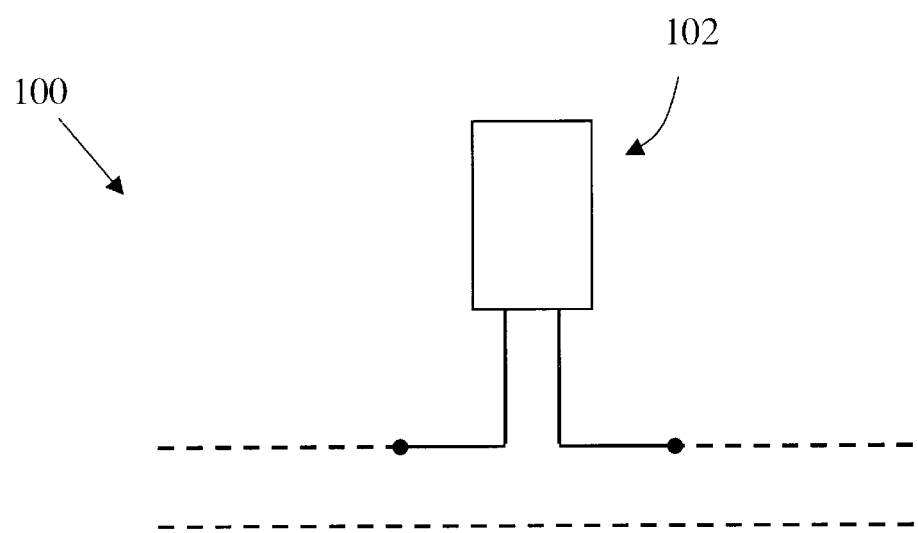
FIGS. 1A–B show exemplary electrical circuits with a transmission line according to embodiments of the present invention.
Figure 1B:
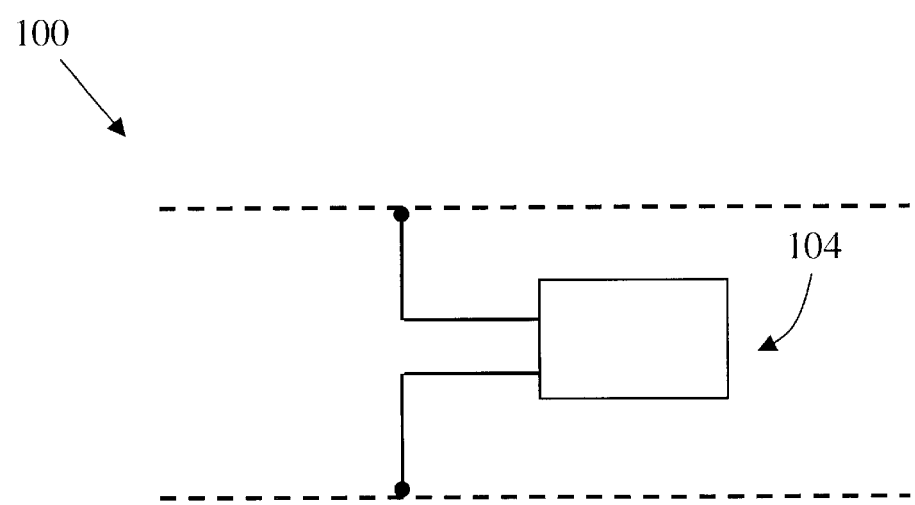

In the design of the MRI receiver coil, the present invention involves an impedance matching element that is build with at least one miniature transmission line cable. FIGS. 1A–B shows electrical circuit 100 that could include at least one miniature transmission line cable. FIG. 1A shows electrical circuit 100 with miniature transmission line cable 102 which is placed in series in electrical circuit 100. FIG. 1B shows electrical circuit 100 with miniature transmission line cable 104 which is placed in parallel in electrical circuit 100. Electrical circuit 100 could include at least one miniature transmission line with different topologies. Each topology could have transmission lines that either have a closed or open circuit as well as transmission lines that either are connected at just one end or at both ends. In addition, electrical circuit 100 could also include standard electrical components, for instance, but not limited to, capacitors, coils, inductors, and resistors. In general, electrical circuit 100 could be any configuration in which an impedance matching element is constructed with electrical specifications that are in accordance with the requirements and specifications of a particular minimally invasive procedure and/or intravascular imaging procedure. Conductive thin film layers are used to form electrically shielded structures for intravascular/catheter MRI coils. These utilize silver painted or coaxial shields to form Faraday shields minimizing surrounding tissue interactions. Thin film sections can also be used to create capacitors.

Figure 2A:
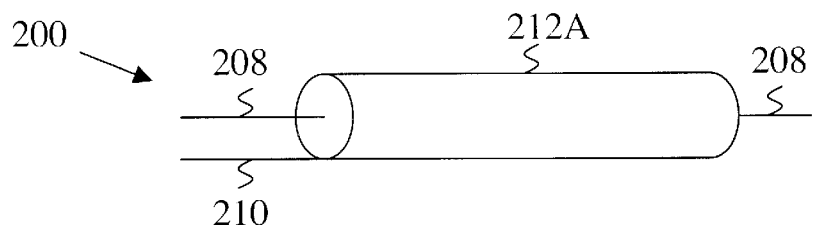
FIGS. 2A–2D show exemplary transmission line cables according to embodiments of the present invention.
Figure 2B:
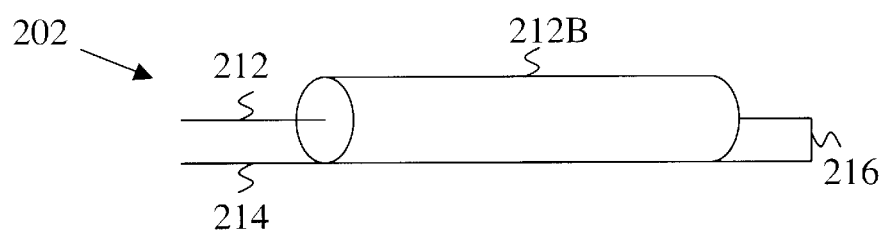
Figure 2C:
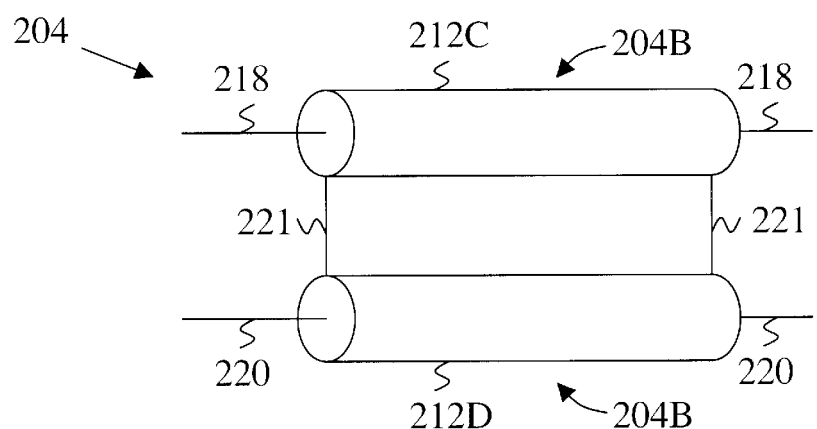
Figure 2D:
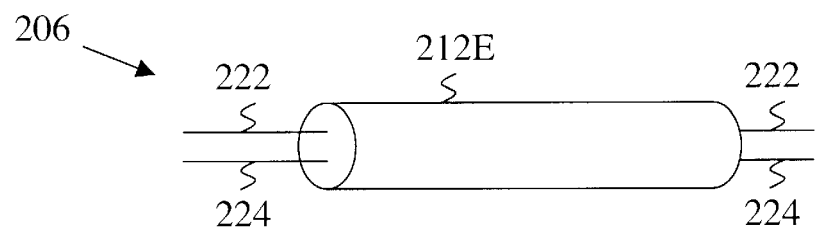

FIGS. 2A–D show exemplary embodiments of different miniature transmission lines. FIG. 2A shows a miniature coaxial cable 200 with a shield 212A and lead 208. Lead 210 in 200 is connected to shield 212A. In this particular example of FIG. 2A, miniature coaxial cable 200 is a coaxial capacitor. Miniature coaxial cable 200 is defined as a capacitance matching element with a capacitance C. The capacitance C of this capacitance matching element is adjustable by adjusting the length of the miniature transmission line cable or miniature coaxial cable. Leads 208 and 210 form two terminal ends of transmission line capacitor 200. FIG. 2B shows a miniature coaxial cable 202 with a shield 212B and lead 212. Lead 212 in 202 is not connected to shield 212B leaving an open circuit. Lead 214 is connected to shield 212B. At the opposite end of miniature coaxial cable 202, lead 212 is connected to shield 212B creating a closed circuit 216. In this particular example of FIG. 2B, miniature coaxial cable 202 is a coaxial inductor. Miniature coaxial cable 202 is defined as a inductance matching element with an inductance L. The inductance L of this inductance matching element is adjustable by adjusting the length of the miniature transmission line cable or miniature coaxial cable. Leads 212 and 214 form two terminal ends of transmission line inductor 202. FIG. 2C shows two miniature coaxial cables 204, which are constructed to create a balanced shield transmission line or balanced coaxial pair. In 204, miniature coaxial cable 204A has lead 218 and shield 212C and miniature coaxial cable 204B has lead 220 and shield 212D. In addition, 204 shows connections 221 of shield 212C of miniature coaxial cable 204A to shield 212D of miniature coaxial cable 204B. In the present invention, balanced and series connected transmission lines are, for instance, used as a means to shield the patient and probe from each other and prevent dangerous common mode current and reduces noise. FIG. 2D shows a transmission line 206 that is constructed as a shielded twin line. Transmission line 206, has two leads 222 and 224 both shielded by shield 212E.

Figure 3A:
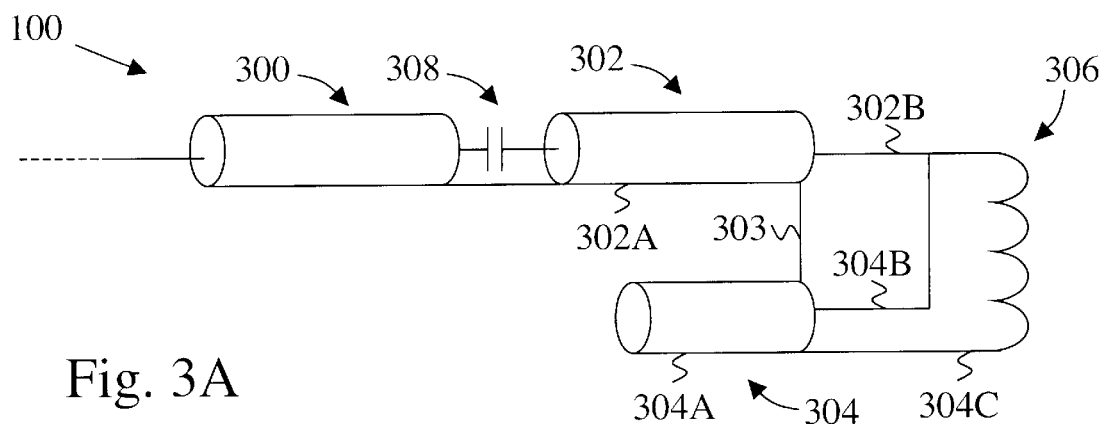
FIGS. 3A–B shows exemplary embodiments of electrical circuits with standard components and transmission lines according to embodiments of the present invention.
Figure 3B:
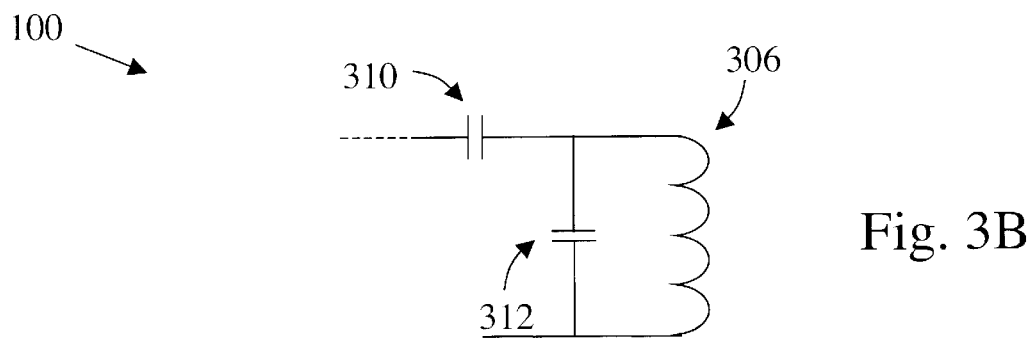

FIGS. 3A–B show exemplary embodiments of electrical circuit 100 in which a combination of standard components is used with miniature transmission line cables or miniature coaxial cables. In FIG. 3A, transmission line cables 300 and 302 are included with different electrical properties, such as length and/or characteristic impedance. Transmission line cables 300 and 302 are fine-tuning elements that are placed in series with an initially constructed impedance matching element or an electrical circuit. These fine-tuning elements are connected at both ends of the transmission line cable. The MRJ receiver coil of the present invention provides hereby a fine-tuning element that is placed remotely. The series connected lines or fine-tuning elements allow fine-tuning to be performed remotely in larger cross-sectional areas. This fine-tuning transmission line could use micro-coaxial cable of different characteristic impedance than nominal 50-ohm cable. FIG. 3A shows transmission line cable 304, which is a coaxial capacitor that is connected to fine-tuning element 302 and coil 306. Shield 304A of coaxial capacitor 304 is connected by lead 303 to shield 302A of fine-tuning element 302. Lead 304C is connected to shield 304A of coaxial capacitor 304. In addition, lead 302B of fine-tuning element 302 is connected to lead 304B of coaxial capacitor 304. Finally, coil 306 is connected to leads 302B of fine-tuning element 302 and 304C of coaxial capacitor 304. Transmission line cable 300 could potentially be connected to a connector or additional electrical circuitry could be added. FIG. 3B shows the electrical equivalent of FIG. 3A wherein capacitor 308 is similar to capacitor 310, although each could have different capacitance values. In addition, FIG. 3B shows the electrical equivalent of capacitor 304 represented by capacitor 312, although each capacitor could have different capacitance values.

Figure 4A:
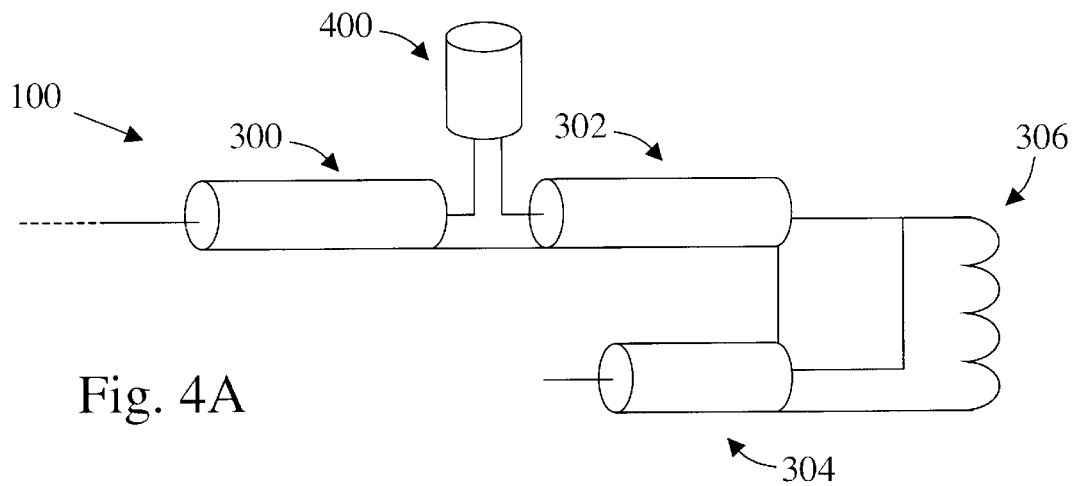
FIGS. 4A–C show exemplary embodiments similar to those of FIGS. 3A–B with the difference that a fixed capacitor is replaced by a transmission line according to an embodiment of the present invention.
Figure 4B:
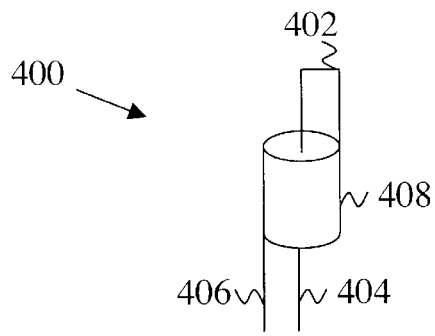
Figure 4C:
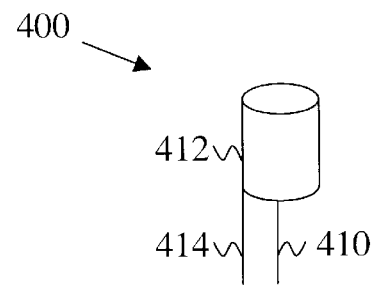

FIGS. 4A–C show exemplary embodiments similar to those of FIGS. 3A–B with the difference that fixed capacitor 308 in FIG. 3A is now replaced by transmission line cable 400 as shown in FIG. 4A. Transmission line cable 400 could be, but is not limited to, a coaxial capacitor, inductor, balanced shielded transmission line or balanced coaxial pair, or a shielded twin lead as shown in FIGS. 2A–D and discussed above. An example of a coaxial inductor is shown in FIG. 4B where 402 is a closed circuit wherein one end of lead 404 is connected to shield 408. However, lead 406 is connected to shield 408 but not connected to lead 404. An example of a coaxial capacitor is shown in FIG. 4C wherein lead 410 is not connected to lead 414, but lead 414 is connected to shield 412.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed is:

1. An MRI receiver coil assembly for catheter procedures, comprising:
   (a) an MRI receiver coil; and
   (b) an impedance matching element connected to said coil, wherein said impedance matching element comprises at least one miniature transmission line cable, and wherein said impedance matching element does not include a lumped circuit element, and wherein said at least one miniature transmission line cable are flexible and locally adjustable.

2. The MRI receiver coil assembly of claim 1, wherein said at least one miniature transmission line cable is at least one miniature coaxial cable.

3. The MRI receiver coil assembly of claim 1, wherein said at least one miniature transmission line cable is an inductance matching element defining an inductance L.

4. The MRI receiver coil assembly of claim 3, wherein said inductance L of said inductance matching element is adjustable by adjusting at least one length of said at least one miniature transmission line cable.

5. The MRI receiver coil assembly of claim 1, wherein said at least one miniature transmission line cable is a capacitance matching element defining a capacitance C.

6. The MRI receiver coil assembly of claim 5, wherein said capacitance C of said capacitance matching element is adjustable by adjusting at least one length of said at least one miniature transmission line cable.

7. The MRI receiver coil assembly of claim 1, wherein said at least one miniature transmission line cable has at least one open circuit.

8. The MRJ receiver coil assembly of claim 1, wherein said at least one miniature transmission line cable has at least one closed circuit.

9. The MRI receiver coil assembly of claim 1, wherein said at least one miniature transmission line cable is surrounded by a shielding element.

10. The MRI receiver coil assembly of claim 1, wherein said at least one miniature transmission line cable is connected in series with said coil.

11. The MRI receiver coil assembly of claim 1, wherein said at least one miniature transmission line cable is connected in parallel with said coil.

12. The MRI receiver coil assembly of claim 1, wherein said impedance matching element comprises conductive thin film layers to form electrically shielded structures.

13. The MRI receiver coil assembly of claim 12, wherein said electrically shielded structures are selected from the group consisting of silver paint and coaxial shields.

14. The MRI receiver coil assembly of claim 12, wherein said electrically shielded structures are Faraday shields to prevent noise and losses from electrical field interactions.

15. The MRI receiver coil assembly of claim 1, wherein said impedance matching element comprises balanced transmission lines to prevent common mode current and reduce noise.

16. The MRI receiver coil assembly of claim 1, further comprising a fine-tuning element wherein said fine-tuning element comprises at least one additional miniature transmission line placed in series with said impedance matching element and connected at both ends placed down towards a part of a coax cable of an MRI scanner.

17. The MRI receiver coil assembly of claim 16, wherein said fine-tuning element has different electrical properties.

18. The MRI receiver coil assembly of claim 16, wherein said fine-tuning element is placed remotely.

19. A method of constructing an MRI receiver coil assembly for catheter procedures, the method comprising:
   (a) providing an MRI receiver coil;
   (b) trimming at least one miniature transmission line cable to provide a impedance matching element, wherein said impedance matching element does not include a lumped circuit element and wherein said at least one miniature transmission line cable are flexible and locally adjustable; and
   (c) connecting said impedance matching element to said coil.

20. The method of claim 19, wherein said at least one miniature transmission line cable is at least one miniature coaxial cable.

21. The method of claim 19, wherein said at least one miniature transmission line cable is an inductance matching element defining an inductance L.

22. The method of claim 21, wherein said inductance L of said inductance matching element is adjustable by adjusting at least one length of said at least one miniature transmission line cable.

23. The method of claim 19, wherein said at least one miniature transmission line cable is a capacitance matching element defining a capacitance C.

24. The method of claim 23, wherein said capacitance C of said capacitance matching element is adjustable by adjusting at least one length of said at least one miniature transmission line cable.

25. The method of claim 19, further comprising surrounding said at least one miniature transmission line cable with a shielding element.

26. The method of claim 19, wherein said connecting comprises connecting said at least one miniature transmission line cable in series with said coil.

27. The method of claim 19, wherein said connecting comprises connecting said at least one miniature transmission line cable in parallel with said coil.

28. The method of claim 19, wherein said impedance matching element further comprises conductive thin film layers to form electrically shielded structures.

29. The method of claim 28, wherein said electrically shielded structures are selected from the group consisting of silver paint and coaxial shields.

30. The method of claim 28, wherein said electrically shielded structures are Faraday shields to prevent noise and losses from electrical field interactions.

31. The method of claim 19, further comprising incorporating in said impedance matching element balanced transmission lines to prevent common mode current and reduce noise.

32. The method of claim 19, further comprising including a fine-tuning element wherein said fine-tuning element comprises at least one additional miniature transmission line placed in series with said impedance matching element being connected at both ends placed down towards a part of a coax cable of an MRI scanner.

33. The method of claim 32, wherein said fine-tuning element has different electrical properties.

34. The method of claim 32, wherein said fine-tuning element is remotely disposed.

* * * * *